(12) United States Patent
Ball et al.

(10) Patent No.: US 6,344,331 B1
(45) Date of Patent: Feb. 5, 2002

(54) WATER IMMISCIBLE SOLVENT BASED BINDING SYSTEMS

(75) Inventors: Raymond Lathan Ball, Haarlem (NL); Jeremy Paul Aston, Cardiff (GB); Jennifer Cryer, Cardiff (GB); Ian Weeks, Cardiff (GB)

(73) Assignee: Molecular Light Technology Research Limited, Wales (GB)

( * ) Notice: Subject to any disclaimer, the term of this patent is extended or adjusted under 35 U.S.C. 154(b) by 0 days.

(21) Appl. No.: 09/147,174

(22) PCT Filed: Apr. 24, 1997

(86) PCT No.: PCT/GB97/01133

§ 371 Date: Oct. 23, 1998

§ 102(e) Date: Oct. 23, 1998

(87) PCT Pub. No.: WO97/40382

PCT Pub. Date: Oct. 30, 1997

(30) Foreign Application Priority Data

Apr. 24, 1996 (GB) .............................. 9608611

(51) Int. Cl.[7] .......................... G01N 33/53; G01N 33/16
(52) U.S. Cl. .............................. 435/7.1; 435/7; 435/7.2; 435/7.21; 435/8; 435/5; 435/6; 435/7.92; 435/7.93; 435/7.94; 435/7.95; 435/968; 435/973; 436/56; 436/60; 436/164; 436/500; 436/536; 436/537; 436/800; 436/805; 436/172; 250/361 C; 250/302; 250/259
(58) Field of Search .............................. 435/7, 7.1, 7.2, 435/7.21, 8, 5, 6, 7.92, 7.93, 7.94, 7.95, 968, 973, 56, 60, 164; 436/500, 536, 537, 800, 805, 172; 250/361 C, 302, 259

(56) References Cited

U.S. PATENT DOCUMENTS 4,238,472 A   12/1980   Albio et al. .................. 424/1
4,761,382 A * 8/1988   Wood Head et al. ....... 436/536
5,656,207 A * 8/1997   Woodhead et al. ......... 252/700
5,879,946 A * 3/1999   Weeks et al. ................. 436/60

FOREIGN PATENT DOCUMENTS

| EP | 11837 | 6/1980 | |
| EP | 327163 | 8/1989 | |
| EP | 0 327 163 A * | 8/1989 | .......... G01N/33/26 |
| GB | 2103790 | 2/1983 | |
| GB | 2 103 790 A * | 2/1983 | .......... G01N/33/58 |
| WO | WO 87/01206 * | 2/1987 | ......... G01N/33/537 |
| WO | WO87/01206 | 2/1987 | |
| WO | WO92/12427 | 7/1992 | .......... G01N/33/53 |

OTHER PUBLICATIONS

Weetal, H.H., "Antibodies in Water Immiscible Solvents, Immobilized Antibodies in Hexane", *Journal of Immunological Methods*, vol. 136, No. 2 Feb. 12, 1991, pp. 139–142.
Russell et al, Biochem Biophys Res Comm 1989 158:80–85.
Francis et al, Analyst 1994 119:1801–1805.
Matsuura et al Biochem 1993, 114:273–278.
Weetall, "Antibodies in water immiscible solvents—Immobilized antibodies in hexane.", Journal of Immunological Methods, vol. 136, No. 1, pp. 139–142, 1991.*

* cited by examiner

*Primary Examiner*—Christopher L. Chin
*Assistant Examiner*—Lisa V. Cook
(74) *Attorney, Agent, or Firm*—Birch, Stewart, Kolasch & Birch, LLP

(57) ABSTRACT

A biphase immunoassay method is provided in which a water immiscible liquid is qualitatively or quantitatively measured by mixing a sample of the water immiscible liquid with an aqueous solution containing a specific binding partner of the analyte. Binding occurs at or across the interface between the respective liquids and the degree of association of the analyte with its binding partner is dependent upon the concentration ratio rather than absolute quantities. The degree of association may be determined and used to determine the presence and/or concentration of analyte in the sample.

19 Claims, 1 Drawing Sheet

WATER IMMISCIBLE SOLVENT BASED BINDING SYSTEMS

This application claims priority based on International application PCT/GB97/01133 filed Apr. 24, 1997, and GB 9608611.1 filed Apr. 24, 1996.

This invention relates to methods and kits for detecting or assaying an analyte present in a water immiscible solvent.

The terms "water immiscible solvent" and "aqueous solution" are intended to be construed broadly, to include liquids which are partially miscible on agitation but which on settling separate into two layers to form a liquid/liquid interface.

BACKGROUND TO THE INVENTION

Ligand binding assays have been applied extensively to the detection and quantisation of compounds of biological importance present in fluids such as serum. Such assays rely on the interaction between the compound to be analysed (the analyte) and a specific binding partner such as an antibody. The extent of the binding reaction is generally monitored by the use of a marker, such as a radioactive label, which can be detected at very low concentrations. These assay techniques have been used widely for the measurement of water soluble substances such as proteins and also in the quantisation of compounds such as steroids or thyroid hormones, which are only sparingly soluble in water but which are normally associated with specific or non-specific binding proteins. Assay of these latter compounds frequently involves extraction of the substance of interest into a water immiscible solvent, removal of the solvent by evaporation and then "solubilisation" of the compound in an aqueous medium to provide essentially a single phase system in which reaction with a binding partner such as an antibody can occur. Such techniques are labor intensive and can only be performed in specialised laboratories.

The progressive devolution of ligand binding assays to non-specialist laboratories and their increasing use in analytical applications outside clinical diagnostics require simplification of the basic analytical procedures to make them accessible to non-specialist staff in what might be regarded as a "field" situation.

It has generally been considered that the assay system should essentially comprise a single liquid phase, and as will be evident from the prior art, complex and expensive procedures have been implemented to render a sample of an analyte soluble in an organic solvent suitable for analysis by ligand binding assays.

However, we have discovered, surprisingly, that an effective ligand binding assay may be set up in a two-phase liquid system in which the binding partner is in an aqueous phase and the analyte is in a substantially water immiscible solvent phase and in which binding takes place at or near the interface between the liquids.

DESCRIPTION OF PRIOR ART

The concept of a physiologically derived molecule such as an antibody retaining its activity under conditions where it is exposed to an organic solvent is both unexpected and unpredictable. Russell et al (Biochem Biophys Res Comm 1989; 158: 80) have shown that immobilised anti-hapten antibodies will bind hapten in the presence of water miscible solvents such as dioxane and acetonitrile. However, their experiments showed that the binding affinity of the antibodies was significantly reduced by the presence of the solvent and also that the binding was progressively reduced as the hydrophobicity of the solvent used was increased.

Subsequently, Weetall (J Immunol Meth 1991; 136:139) found that antibodies linked to paramagnetic particles were capable of retaining binding activity in water immiscible solvents such ar hexane.

Francis and Craston (Analyst 1994; 119:1801) developed an immunoassay for parathion in hexane in which the antibody was encapsulated in reverse micelles. In this way, the antibody was "protected" by inclusion in the micelle.

Recently, Matsuura et al (J Biochem 1993; 114:273) have described the binding of a shell fish toxin to antibodies in the presence of methanol, though they did not develop a quantitive analytical procedure.

U.S. Pat. No. 4,238,472 describes a method in which samples are extracted with a water immiscible solvent which is subsequently removed by evaporation. The dried residues are taken up in a detergent which will form an emulsion with the assay reagents, essentially producing a single phase liquid system.

Published PCT Application No. WO 92/12427 describes an assay procedure where the sample is extracted into hexane and, after further purification, the hexane is removed by evaporation and the sample re-dissolved into a water soluble solvent (methanol). This is then diluted into an aqueous assay buffer, again forming a single phase.

SUMMARY OF THE INVENTION

Broadly speaking, the present invention relates to the detection and quantisation of largely water insoluble compounds dissolved in a water immiscible solvent by being brought into contact with a specific binding reagent present in an aqueous medium so that a binding reaction takes place via the water/solvent interface, the extent of the binding reaction, i.e. the degree of association between said analyte and said binding partner being proportional to the concentration of compound in the solvent phase.

Thus, in one aspect of this invention, there is provided a method of determining the presence and/or concentration of an analyte in a substantially water immiscible solvent, which method comprises the steps of:

(i) mixing a sample of the water immiscible solvent with an aqueous solution containing a specific binding partner of said analyte to allow binding between said binding partner and said analyte (if present), and (ii) monitoring directly or indirectly the degree of association between said analyte and said binding partner thereby to determine the presence and/or concentration of said analyte.

The benefits of this method include the facts that the method provides a two phase liquid system in which binding can occur and that the binding partner is largely preserved or protected by remaining in the aqueous phase, and the natural separate of the aqueous and solvent phases may in many cases simplify separation of the fractions of the bound and unbound analyte.

In a preferred aspect, the binding reagent is an antibody labelled with a substance which allows the extent of binding to be readily assessed.

Preferred embodiments of the present invention allow the development of quantitative or qualitative analytical methods for the detection of hydrophobic compounds present in water immiscible solvents such as hexane, xylene and toluene where the appropriate binding reagent in an aqueous medium is agitated with the solvent sample such that the compound reacts with the binding reagent at or near the water/solvent interface and so becomes effectively "trapped" by the reagent in the aqueous layer. The amount that is trapped in this way is a function of the concentration of analyte in the solvent sample and can be readily determined by standard ligand binding techniques, suitable examples of which are well known to those skilled in the art.

It will be readily appreciated that this approach represents a significant simplification for detecting or assaying an analyte initially present in a solvent, when compared with methods which require prior extraction of the sample or the manufacture of reverse micelles to encapsulate the binding reagent. Such considerations are particularly important when a method is being developed for field use.

In a preferred aspect, the invention involves the use of monoclonal antibodies in solution in an aqueous buffer which are shaken with a sample of a hydrophobic hapten present in a water immiscible solvent. The antibodies, which may be labelled with a marker, are specific for the hapten which will not normally partition into the aqueous phase. After shaking for a predetermined period of time, the mixture is allowed to stand briefly to allow the aqueous and water immiscible solvent layers to separate. The aqueous layer is transferred to a reaction tube which contains an immobilised derivative of the analyte. In a further reaction, labelled antibody which has not reacted with analyte in the sample will bind to the derivative in the tube. The amount of this bound antibody, which varies inversely with the concentration of analyte in the original solvent sample, can be quantified by an appropriate means after it has been washed free of any unreacted antibody. The amount of analyte present in the initial sample can be calculated by reference to reactions of calibrator solutions.

This procedure provides several unique advantages particularly in relation to the establishment of field tests. Firstly, the fact that the binding reagent is free in solution and not immobilised allows for the maximum reaction rate with antigen when the two solutions are agitated together. In practice a reaction time of only one minute may be sufficient to produce significant binding. Secondly, the rate of reaction is concentration dependent so that the measurement of an exact volume of sample is not critical. The avoidance of complex pipetting steps is highly desirable for field testing.

It will also be readily appreciated that simple adaptations of the basic procedure can provide flexibility in the choice of reagents. For example, in another aspect of this invention, it is possible to react an aqueous solution containing unlabelled antibody with the water immiscible analyte solution and then react the aqueous phase with the solid phase analyte as before. After a simple wash, the amount of antibody bound to the solid phase may be detected by means of a further reaction with labelled anti-immunoglobulin antibody. This approach is particularly valuable when only polyclonal antibodies are available, since these may require a complex purification step if they are themselves to be labelled directly.

In another aspect of this invention, a simultaneous reaction for a fixed time period may be performed between labelled antibody in aqueous solution, a water immiscible analyte solution, and the immobilised derivative in a single tube. Once again, the amount of label which becomes associated with the solid phase varies inversely with the concentration of analyte in the solvent sample. This approach adds to the simplicity of the test format, which in turn makes the method suitable for field or laboratory applications.

Though the methods of this invention have been designed for the detection of water insoluble compounds, it is appreciated that the invention can be readily applied even to substances which show some partitioning into aqueous media, on the basis that the degree of partitioning and ultimately of uptake by the binding reagent will still be proportional to the concentration of compound in the solvent. In such a situation, the binding reagent effectively "traps" the analyte as it transfers from the water immiscible phase to the aqueous phase at the interface. Thus, the method is not restricted in the types of molecule to which it can be applied so long as the analyte substance is present in, or can be extracted into a water immiscible solvent.

There are many important potential applications of this invention. One such application is the identification and quantisation of organic residues present in materials such as soil and water. Pesticides used in agriculture can be difficult to trace in the environment. Moreover, conventional analytical procedures such as mass spectrometry may lack the required sensitivity and in any case are inherently complex. The ability to extract such materials into water immiscible solvents and then quantify them directly by immunoassay provides a simple and general approach to monitoring the presence of potentially toxic compounds present in samples which do not lend themselves readily to analysis by conventional procedures.

The use of solvents for the extraction of analytes from samples such as, for example but without limitation, soil, seeds, foliage and the like, is well-known to those skilled in the art. Such procedures are represented by, for example but without limitation, solvent partitions, the use of solid adsorbents, chromatographic methods and super-critical fluid extraction. The choice of materials and methods for such purposes are well-established and it is well within the scope of one skilled in the art to choose a method appropriate for a particular sample type and analyte.

Thus, in another aspect of this invention, there is provided a method of detecting the presence and/or concentration in a sample of an analyte which is at least partially soluble in a water immiscible solvent, which comprises the steps of:
  (i) contacting the sample with said water immiscible solvent to extract said analyte therefrom;
  (ii) collecting the water immiscible solvent with any extracted analyte solution;
  (iii) mixing said collected water immiscible solvent with an aqueous solution containing a specific binding partner of said analyte to allow binding between said binding partner and said analyte (if present), and
  (iv) monitoring directly or indirectly the degree of association between said analyte and said binding partner, thereby to determine the presence and/or concentration of said analyte.

For example, it is difficult to quantify herbicides such as atrazine when they are present at concentrations below 100 ng/ml using conventional chemical approaches. In contrast, a simple immunoassay procedure which can be carried out in less than 10 minutes can yield a sensitivity of detection which is better than 1 ng/ml.

Another important application relates to the ability to identify specifically a manufacturer's own product in order to combat counterfeiting, as described by Wraith and Britton in EPA 0327163. That application describes the use of compounds which could be added to petroleum based fuels prior to their distribution and subsequently extracted from samples, taken at different points in the distribution process, into an aqueous medium suitable for detection by immunoassay.

In another aspect, this invention provides a means for the direct detection by immunoassay of water immiscible components added to fuel as marker substances. Alternatively, it can be applied to the quantisation of certain additives which are introduced into the fuel to enhance its performance, provided a suitable binding partner for such an additive can be identified. Since certain of these so-called additives are unique to a particular manufacturer, their quantitative assay in this way provides a means of identifying the specific product as well as a means of controlling the quality of the end product to the consumer.

It will be readily appreciated that the ease of use provided by a direct test which does not require complex sample manipulations enables such a test to be performed essentially under field conditions.

The identification of the analyte in question is carried out by means of a specific binding partner such as an antibody. It is appreciated by those skilled in the art that both polyclonal and, more usefully, monoclonal antibodies can be produced to a very wide range of organic compounds. Antibodies can be labelled with a variety of markers such as radioisotopes, enzymes or fluorescent molecules.

In a preferred aspect of this invention, antibodies are labelled with chemiluminescent molecules, preferably acridinium derivatives as described in EP 0082636. Such compounds have several unique advantages for this type of application. Firstly, they can be detected with extremely high sensitivity, thus contributing to the overall sensitivity of the method. Secondly, chemiluminescent molecules are inherently stable until the chemical reaction leading to photon emission is triggered. Thus they can be introduced into a wide range of liquid media without risk of losing chemiluminescence activity.

The analytical procedure can be pursued in a variety of formats as described above. In each case the methods use the fact is that the degree to which the labelled antibody binds to the solid phase derivative is dependent upon the concentration of analyte in the solvent sample. By measuring the degree of binding produced with known analyte concentrations, a calibration curve can be produced to allow the quantisation of unknown samples of the analyte.

Attention has been drawn to one advantage of this type of procedure in that it can be undertaken without the need for complex pipetting steps. Moreover, the light measurement can be carried out with simple, readily available luminometers. Portable instruments are presently available so that in combination with these simplified analytical procedures, it is possible to develop highly sensitive tests for use under field conditions.

Whilst the invention has been described above, it extends to any inventive combination of features set out above or in the following examples.

EXAMPLES

Figures 1, 2:
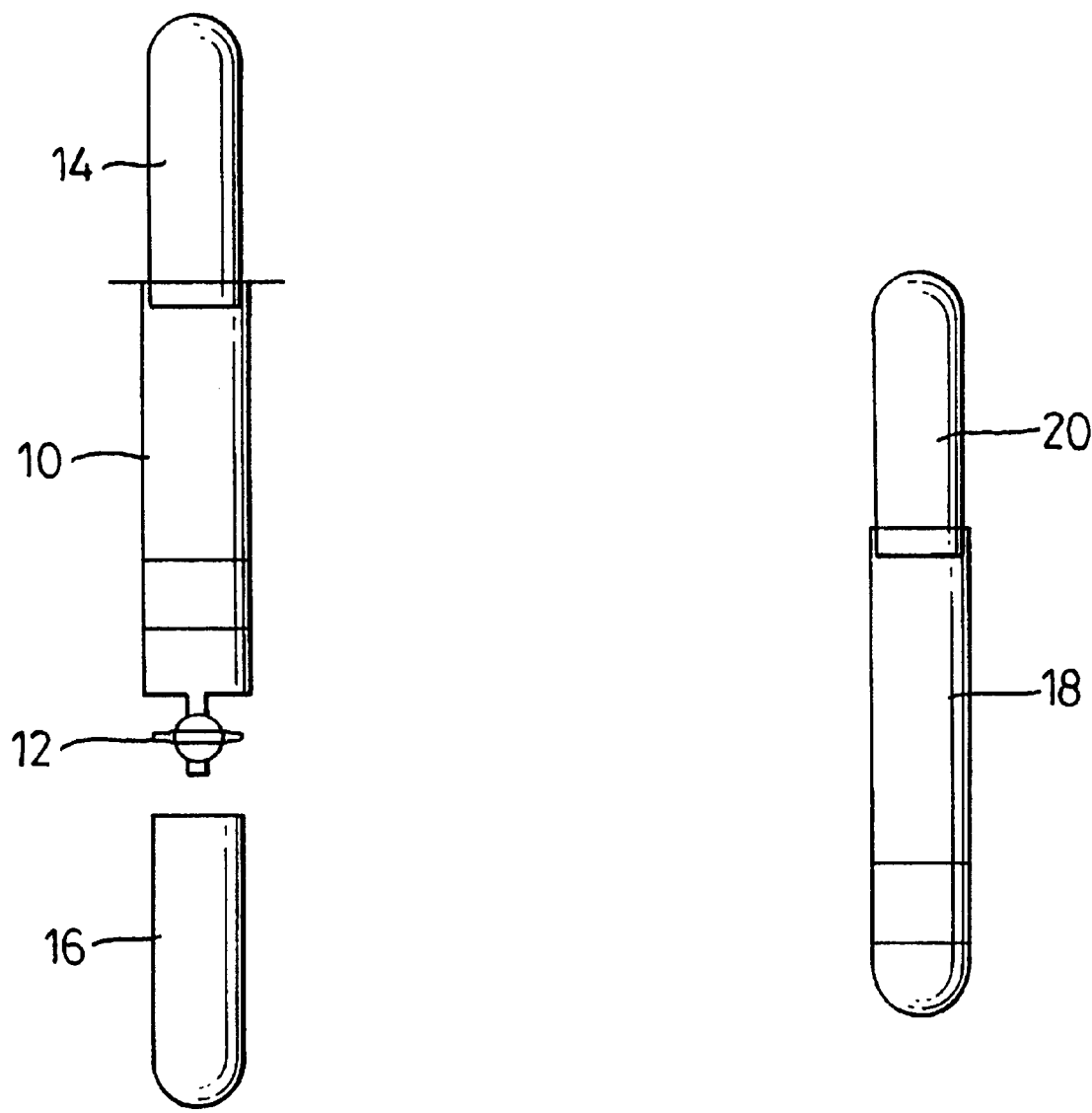
FIG. 1 is a schematic view of a combination of a test tube and a syringe used in Example 5.
FIG. 2 is a schematic view of an arrangement of test tubes used in Example 6.

The following examples are given by way of illustration and not limitation.

Example 1

Chemiluminescent Immunoassay for Atrazine in Hexane Extracts
(a) Preparation of a Derivative of Atrazine In order to attach atrazine to a protein, it was initially converted to 3-{{4-(ethylamino)-[(1-methylethyl)amino]-1, 3,5-triazine-2-yl}thio}propanoic acid by the method of Goodrow et al (J Agric Food Chem 1990; 38: 4990). Briefly, a solution of atrazine in dry ethanol was refluxed under nitrogen with 3-mercaptopropionic acid for 3 hours. The soluble product of this reaction was transferred to a clean vessel and the solvent evaporated under vacuum. The residue was taken up in 25 ml of 5% (w/v) sodium hydrogen carbonate and washed three times with chloroform. The propanoic acid derivative was then precipitated by acidification of the solution with 6N hydrochloric acid, washed with water and dried. The structural composition of the product was assessed by NMR spectroscopy and found to be consistent with published data.

(b) Preparation of a Protein-Atrazine Conjugate

The atrazine derivative was conjugated to bovine serum albumin (BSA) by the method of Goodrow et al. Briefly, equimolar quantities of the derivative and succinic anhydride were reacted for 3 hours with a 10% molar excess of dicyclohexylcarbodiimide in dry dimethylformamide (DMF). The precipitate of dicyclohexylurea was removed by passing the slurry through a column containing glass wool and 0.25 ml of the eluate mixed with a 0.01% (w/v) solution of BSA in water (5 ml) and DMF (1.05 ml). The reaction was allowed to proceed for 22 hours and the product was extensively dialysed against phosphate buffered saline (PBS), pH 7.4, 0.01 M.

(c) Preparation of Coated Tubes

Polystyrene tubes (Nunc Maxisorb™) were coated with the atrazine-BSA conjugate in 0.1 M bicarbonate buffer at pH 9.6 for 18 hours. The tubes were washed 3 times with PBS containing 0.5% (v/v) Tween 20 (PBS/Tween) and then exposed to a solution of 0.1% (w/v) BSA in PBS/Tween with 0.05% (w/v) sodium azide as a preservative. The blocking solution was aspirated and tubes were dried under vacuum and then stored dry until used.

(d) Preparation of Labelled Antibody

Affinity purified goat (anti-rabbit immunoglobulin) antibody was purchased from Sigma Chemical Co and labelled with an active acridinium ester as described in EP 0082636. Labelled antibodies were purified by gel filtration and stored in aliquots at −20° C.

(e) Atrazine Immunoassay

Standard concentrations of atrazine were made up in hexane. Immunoextraction was accomplished by mixing 1 ml of each with an equal volume of PBS/Tween containing rabbit anti-atrazine antibody (obtained from Biodesign International, Maine 04043, U.S.A.) at a concentration of 2.35 µg/ml for 1 minute by manual inversion. The liquid layers were allowed to separate and 0.5 ml of the lower (aqueous) layer were transferred to conjugate-coated tubes. After 5 minutes, the reaction was stopped by rinsing the tubes 3 times with PBS/Tween. Acridinium ester labelled goat (anti-rabbit immunoglobulin) antibody was added to each tube and after a further 15 minutes, the tubes were rinsed again in PBS/Tween. Luminescence was quantified in a luminometer during a 2 second reaction initiated in the luminometer using Reagents 1 and 2 (Chiron Diagnostics, Halstead, Essex, U.K.) according to the manufacturer's instructions. The relationship between light output and the concentration of atrazine in the samples is shown below, from which it will be seen that the mean light output varies inversely with the concentration of atrazine, and that the assay allows detection of parts per billion.

| Concentration of atrazine in hexane (ng/ml) | Mean Light Output (relative light units) |
|---|---|
| 0 | 939,215 |
| 1 | 759,265 |
| 2 | 702,805 |
| 10 | 505,260 |
| 25 | 348,890 |
| 50 | 276,650 |
| 100 | 191,030 |
| 200 | 136,495 |
| 300 | 115,400 |

Example 2

Chemiluminescent Immunoassay for Atrazine in Dodecane Extracts

The procedure described in Example 1 was adapted to demonstrate the ability of the method to be applicable to other water immiscible solvents. Here the procedure was essentially the same as Example 1 except that atrazine was dissolved in dodecane as opposed to hexane. The relationship between the atrazine concentration in the dodecane and the light output as measured in the luminometer is shown below:

| Concentration of Atrazine in dodecane (ng/ml) | Mean light output (relative light units) |
|---|---|
| 0 | 960790 |
| 0.1 | 753860 |
| 0.2 | 612000 |
| 0.5 | 527240 |
| 1 | 462170 |
| 5 | 314510 |
| 10 | 219730 |

Example 3

Chemiluminescent Immunoassay for Simazine in Hexane Extracts

The procedure described in Example 1 was adapted to demonstrate the ability of the method to be applicable to other organic soluble substances. Here the procedure and reagents were essentially the same as Example 1 except that simazine was dissolved in hexane. The relationship between the simazine concentration in the hexane and the light output as measured in the luminometer is shown below:

| Concentration of simazine in hexane (ng/ml) | Mean light output (relative light units) |
|---|---|
| 0 | 1301735 |
| 0.1 | 1117955 |
| 0.5 | 747565 |
| 1 | 596375 |
| 5 | 574135 |
| 10 | 449360 |

Example 4

Chemiluminescent Immunoassay for a Hydrophobic Molecule ($R_x$)

A hydrophobic hapten $R_x$ having a molecular weight of approximately 350 daltons was selected for its hydrophobic nature (octanol : water partition coefficient, log $K_{ow}$=6.14). A carboxylic acid derivative of the hapten was conjugated to BSA according to the procedure described in Example 1 (b) and the conjugate used at a concentration of 20 μg/ml to coat polystyrene tubes as described in Example 1(c). As before, the tubes were washed and vacuum dried.

A mouse monoclonal antibody directed to $R_x$ was prepared by standard procedures well known to those skilled in the art and was purified by Protein G Sepharose™ affinity chromatography. This antibody was labelled with an acridinium ester as described in EP 0082636 and purified by gel filtration.

Standard solutions were prepared by dissolving known amounts of $R_x$ in commercial diesel fuel to give a range of standard solutions of concentrations from 0 to 20 ppm. The labelled monoclonal antibody was diluted to yield 360×10⁶ RLU/ml light emission.

4 ml of each standard solution were mixed by manual inversion with 1 ml of the diluted labelled antibody solution for 1 minute. After allowing the two liquid phases to separate, 0.5 ml of the aqueous layer were transferred to a coated polystyrene tube and, after a further five minutes, the solution was aspirated and the tubes washed and blotted to remove surplus liquid. The chemiluminescence activity associated with the tube was measured in a luminometer. Data following initiation in the luminometer(using Reagents 1 and 2 (Chiron Diagnostics, Halstead, Essex, U.K.) according to the manufacturer's instructions) based on duplicate readings are given below, from which it will be seen that the mean light output varies inversely with concentration of $R_x$, and that the assay provides sensitivities well in excess of parts per million.

| Concentration of $R_x$ (ppm) | Mean Light Output (Relative Light Units) |
|---|---|
| 0 | 4,141,825 |
| 2.5 | 2,122,660 |
| 5 | 1,420,225 |
| 10 | 734,125 |
| 20 | 427,910 |

In this Example the molecule $R_x$ is a proprietary fuel additive whose exact structure is immaterial in this instance as the purpose of the example is to show that it is possible to measure extremely accurately the concentration of an analyte in an organic liquid such as diesel fuel by raising antibodies to the analyte and using the methods as described herein.

Example 5

Method for Performing Immunoextraction in Immunoassay

Reagents used in an immunoassay for atrazine in hexane were as described in Example 1. Referring to FIG. 1, immunoextraction was performed by dispensing 1 ml of hexane sample containing atrazine into a 5 ml polypropylene syringe 10 fitted with a tap 12. The anti-atrazine antibody in its buffer medium had been previously dispensed into a polypropylene test tube 14 such that the contents of the test tube 14 could be poured into the syringe 10 and the empty test tube 14 used as a closure for the top of the syringe 10 to form an assembly shown in FIG. 1. Immunoextraction was performed by repeated inversion of the assembly for one minute, followed by standing in an upright position with the syringe lowermost until the two layers separated. The test tube 14 was then removed and the tap opened so as to allow the bottom layer only to be dispensed into a conjugate-coated tube 16. The remainder of the assay was performed as described in Example 1.

Example 6

Simplified Method for Performing Immunoextraction in Immunoassay

Reagents used in an immunoassay for atrazine in hexane were as described in Example 1. Referring to FIG. 2, immunoextraction was performed by dispensing 1 ml of hexane sample containing atrazine into a 10 ml polypropylene test tube 18 fitted with a stopper (not shown). The anti-atrazine antibody in its buffer medium had been previously dispensed into this test tube 18. Immunoextraction was performed by repeated inversion of the stoppered test tube 18 for one minute. The stopper was then removed and the mouth of a conjugate-coated test tube 20 inserted into the polypropylene tube 18 so as to form the assembly shown in FIG. 2. The assembly was inverted such that the aqueous layer was allowed to contact the "active" surface of the conjugate coated tube 20. The assembly was allowed to stand in this position for 5 minutes following which it was re-inverted. The conjugate-coated tube was removed from the assembly and processed further as described in Example 1.

The invention also extends to suitably packaged test kits particularly though not exclusively intended for the field, for use in implementing the above assay methods. In one aspect, a kit for detecting an analyte in a sample of water immiscible liquid may comprise a first container storing an aqueous solution containing a specific binding partner of said analyte, a second container for receiving said sample of water immiscible liquid together with said aqueous solution and for allowing the aqueous fraction to be drawn off, and a third container incorporating immobilised analyte or a derivative thereof. The second container may conveniently be a syringe with a tap or other controllable fluid outlet at its lower end.

In another aspect, the kit may comprise a first container containing a aqueous solution containing a specific binding partner of the analyte and for receiving said sample, and a second container incorporating immobilised analyte or a derivative thereof.

The kits are preferably used in conjunction with a labelled binding partner of the analyte and a portable luminometer. Where it is intended to extract the analyte from a sample using a solvent, the kit may include a container containing a suitable extraction solvent.

What is claimed is:

1. A method of determining the presence and/or concentration of an analyte in a substantially water immiscible liquid, which method comprises the steps of:
   (i) mixing a sample of the water immiscible liquid with an aqueous solution containing a specific binding partner of said analyte to allow binding between said binding partner and analyte present in said water immiscible liquid, and
   (ii) monitoring directly or indirectly the binding between said analyte and said binding partner, thereby to determine the presence and/or concentration of said analyte.

2. A method according to claim 1, wherein said analyte is insoluble in water.

3. A method according to claim 1, wherein said analyte is soluble in water.

4. A method according to claim 1, wherein, following mixing, the water immiscible liquid and the aqueous solution are allowed to separate to form an aqueous/immiscible liquid interface across which the binding partner may bind the analyte.

5. A method according to claim 1, wherein the water immiscible liquid and the aqueous solution are left in mutual contact with each other for a predetermined period before the degree of association is monitored.

6. A method according to claim 1, in which the analyte is an organic compound.

7. A method according to claim 6, wherein said water immiscible liquid is a petrochemical product and the analyte is a marker or additive substance.

8. A method according to claim 7, wherein said petrochemical product is selected from the group comprising gasoline, diesel and lubricant.

9. A method according to claim 1, wherein the specific binding partner is an antibody.

10. A method according to claim 9, wherein the antibody is a monoclonal antibody.

11. A method according to claim 1, wherein after mixing and binding of the analyte (if present) to the specific binding partner, the bound and unbound fractions of said binding partner are separated.

12. A method according to claim 11, wherein after mixing, the mixture is contacted with immobilised analyte or a derivative thereof, to immobilise the unbound fraction of said binding partner, the bound fraction is removed and the amount of said immobilised unbound fraction is determined.

13. A method according to claim 1, wherein the sample of the water immiscible solvent and the aqueous solution are mixed in the presence of immobilised analyte or a derivative thereof.

14. A method according to claim 1, wherein the specific binding partner is labelled with a chemiluminescent compound.

15. A method according to claim 1, wherein said specific binding partner of said analyte comprises an antibody and the bound fraction is monitored by means of a labelled anti-immunoglobulin antibody.

16. A method of detecting the presence and/or concentration in a sample of an analyte which is at least partially soluble in a water immiscible solvent, which comprises the steps of:
   (i) contacting the sample with said water immiscible solvent to extract said analyte therefrom;
   (ii) collecting the water immiscible solvent with any extracted analyte solution;
   (iii) mixing said collected water immiscible solvent with an aqueous solution containing a specific binding partner of said analyte to allow binding between said binding partner and any said analyte present in said water immiscible solvent, and
   (iv) determining directly or indirectly the binding between said analyte and said binding partner thereby to determine the presence and/or concentration of said analyte.

17. A method according to claim 16, wherein said sample comprises a soil sample.

18. A method according to claim 16, wherein said sample comprises a seed.

19. A method for the qualitative or quantitative analysis of an organic compound present in a water immiscible solvent comprising mixing a sample of the water immiscible solvent containing said organic compound with an aqueous solution containing a specific binding partner of said organic compound for a fixed period of time such that said compound binds with said binding partner in a concentration-dependent manner, and determining directly or indirectly the binding between said analyte and said binding partner.

* * * * *